United States Patent [19]

Raitt et al.

[11] Patent Number: 5,554,165
[45] Date of Patent: Sep. 10, 1996

[54] SURGICAL BLADE AND HUB

[75] Inventors: Scott Raitt, Thousand Oaks, Calif.; Donald E. Culveyhouse, Union, Mich.

[73] Assignee: Hall Surgical, Div. of Zimmer, Inc., Largo, Fla.

[21] Appl. No.: 386,044

[22] Filed: Feb. 9, 1995

[51] Int. Cl.⁶ .................................................. A61B 17/14
[52] U.S. Cl. ...................... 606/176; 606/178; 606/179; 403/348; 403/349; 30/340; 30/342
[58] Field of Search ............................. 606/176, 178, 606/179, 82; 403/348, 349; 30/340, 342

[56] References Cited

U.S. PATENT DOCUMENTS

| | | | |
|---|---|---|---|
| 2,557,364 | 6/1951 | Treace | 606/178 |
| 3,905,374 | 9/1975 | Winter | 128/317 |
| 3,943,934 | 3/1976 | Bent | 128/317 |
| 4,036,236 | 7/1977 | Rhodes, Jr. | 128/317 |
| 4,252,121 | 2/1981 | Arnegger | 128/317 |
| 4,285,129 | 8/1981 | Hoffman | 30/392 |
| 4,386,609 | 6/1983 | Mongeon | 128/317 |
| 4,513,742 | 4/1985 | Arnegger | 128/317 |
| 4,532,672 | 8/1985 | Anderson | 403/349 |
| 4,584,999 | 4/1986 | Arnegger | 128/317 |
| 4,617,930 | 10/1986 | Saunders | 128/317 |
| 4,637,391 | 1/1987 | Schlein | 128/317 |
| 4,768,504 | 9/1988 | Ender | 128/317 |
| 4,872,452 | 10/1989 | Alexson | 128/92 |
| 5,042,983 | 8/1991 | Rayhack | 606/87 |
| 5,087,261 | 2/1992 | Ryd et al. | 606/82 |
| 5,092,869 | 3/1992 | Waldron | 606/82 |
| 5,112,299 | 5/1992 | Pascaloff | 604/22 |
| 5,122,142 | 6/1992 | Pascaloff | 606/82 |
| 5,133,728 | 7/1992 | Petersen | 606/176 |
| 5,135,533 | 8/1992 | Petersen et al. | 606/176 |
| 5,176,685 | 1/1993 | Rayhack | 606/87 |
| 5,178,626 | 1/1993 | Pappas | 606/178 |
| 5,263,972 | 11/1993 | Evans et al. | 606/176 |
| 5,468,247 | 11/1995 | Matthai et al. | 606/178 |

*Primary Examiner*—Michael Powell Buiz
*Assistant Examiner*—Kevin Truong
*Attorney, Agent, or Firm*—Todd A. Dawson; Gene Warzecha

[57] ABSTRACT

The surgical saw blade and hub of this invention includes a saw blade and instrument hub which connect the saw blade to the instrument such that no portion of the instrument extends beyond the blade. The blade includes a washer having a plurality of radially extending slots in communication with the central bore of the washer. Alternating slots of the washer are truncated or otherwise do not fully extend through the washer. The truncated slots form shoulders or lans within the washer. The center opening of the washer is in alignment with a base opening in the blade and accommodates a hub from the powered instrument. The hub of the powered instrument includes a plurality of radial fins extending outwardly therefrom. The fins abut against the shoulders of the washer to lock the blade to the hub. A helical spring is provided to maintain pressure against the blade and thereby retain the blade and hub in a locked configuration.

9 Claims, 9 Drawing Sheets

SURGICAL BLADE AND HUB

FIELD OF THE INVENTION

This invention relates to a connection mechanism for a surgical saw blade used in orthopaedic surgery and has specific relevance to a surgical saw blade having a unique locking mechanism.

BACKGROUND OF THE INVENTION

Surgical saw blades commonly used in orthopaedic surgery to cut bone are generally connected to a powered surgical instrument through some type of clamping arrangement wherein a portion of the blade is clamped between portions of the instrument. Therefore, a portion of the instrument is positioned on each side of the blade. If the surgical site is large enough, as would be the case in a hip or knee joint replacement, this is generally not a problem. However, if the surgery involves the small bones in the hand or is maxillofacial or otherwise involves small bones and a small surgical sight, space is at a premium. Having a clamp member extending beyond the hub of the blade may be undesirable and make the instrument difficult to use.

SUMMARY OF THE INVENTION

The surgical saw blade and hub of this invention solves the problem stated above by providing a saw blade and instrument hub which connects the saw blade to the instrument such that no portion of the instrument substantially extends beyond the blade. The blade includes a washer having a plurality of radially extending slots in communication with the central bore of the washer. Alternating slots of the washer are truncated or otherwise do not fully extend through the washer. The truncated slots form shoulders or lands within the washer. The center opening of the washer is in alignment with a base opening in the blade and accommodates a hub from the powered instrument. The hub of the powered instrument includes a plurality of radial fins extending outwardly therefrom. The fins abut against the shoulders of the washer to lock the blade to the hub. A helical spring is provided to maintain pressure against the blade and thereby retain the blade and hub in a locked configuration.

In an alternative embodiment of the invention, the hub is formed having a plurality of slots formed about the hub. Alternating slots terminate adjacent the distal end of the hub. In the alternative embodiment, the blade is formed having an opening through the base. A plurality of teeth extend into the opening and are shaped to be accommodated by the slots in the hub.

In the preferred embodiment, the blade is locked to the drive shaft by a lateral shifting of the drive shaft as influenced by a rotatable collet. When the drive shaft is shifted into a locked position for use, the shaft pulls the blade against a pressure plate which prevents the blade from being removed. In an unlocked position, the drive shaft is shifted outwardly relative to the housing which spaces the blade from the pressure plate. So positioned, the blade may be removed from the drive shaft.

Accordingly, it is an object of the invention to provide for a novel locking mechanism for a surgical blade.

Another object of the invention is to provide for a blade having a base portion having a plurality of radial slots.

Another object of the invention is to provide a hub for a powered oscillation surgical device.

Another object of the invention is to provide for a powered surgical instrument wherein the drive shaft of the instrument is shiftable between a locked and unlocked position to prevent removal of the blade when the shaft is in a locked position.

Another object of the invention is to provide a novel blade locking mechanism for a powered surgical instrument.

Other objects of the invention will become apparent upon a reading of the following description taken with the accompanying drawings.

DESCRIPTION OF THE PREFERRED EMBODIMENTS

The preferred embodiments herein described are not intended to be exhaustive or to limit the invention to the precise forms disclosed. Rather, they are chosen and described to best explain the invention so that others skilled in the art might utilize their teachings.

Referring to FIGS. 1–7, blade 10 is illustrated as including a toothed end 12 and a base end 14. As illustrated, base end 14 includes a circular opening 16. A washer or ring 18 is connected to base end 14 by rivets (not shown) or resistance welding. Alternatively, washer 18 could be integrally formed with blade 10 or molded thereto. Washer 18 could be formed by a number of known methods such as injection molding or powder molding. The important feature regardless of manufacturing technique would be that base end 14 and washer 18 are rigidly secured together. Washer 18 includes an interior face 20 and an exterior face 22 relative to base end 14 (See FIG. 7). As illustrated washer 18 includes a central opening 24 with a plurality of slots 26' and 26" extending radially from the central opening in alternating fashion. Each slot 26' extends fully from the interior face 20 through the exterior face 22. As shown best in FIG. 7, each slot 26" extends from the interior face 20 toward the exterior face 22 but is truncated so as to form a shoulder 28 adjacent exterior face 22.

Figure 1:
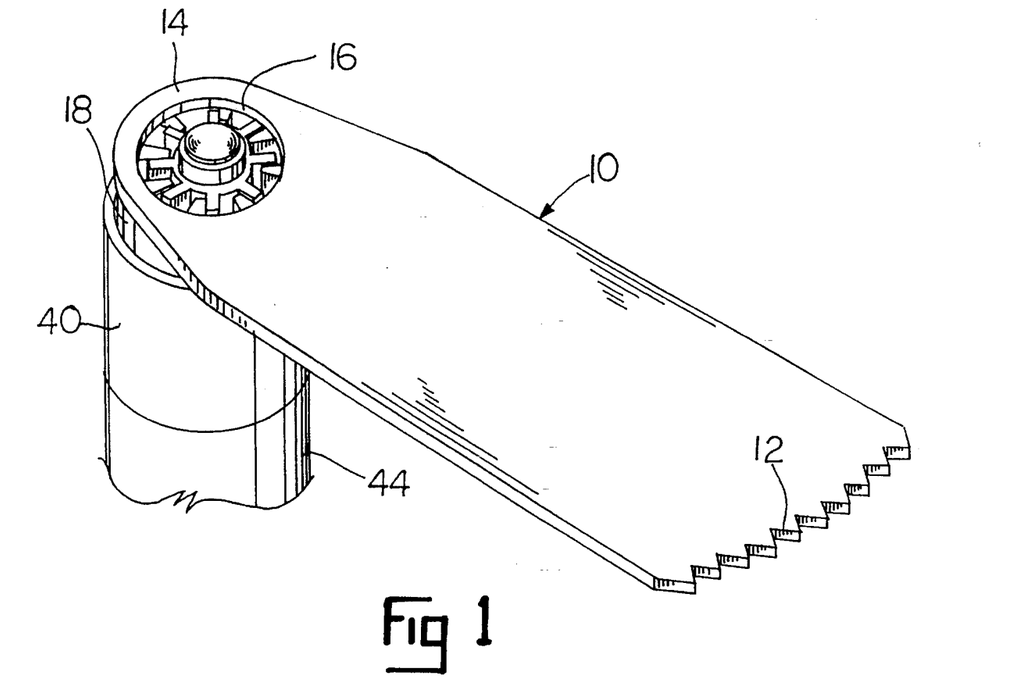
FIG. 1 is a perspective view of the blade and hub of the invention with the blade connected to the hub.
Figure 2:
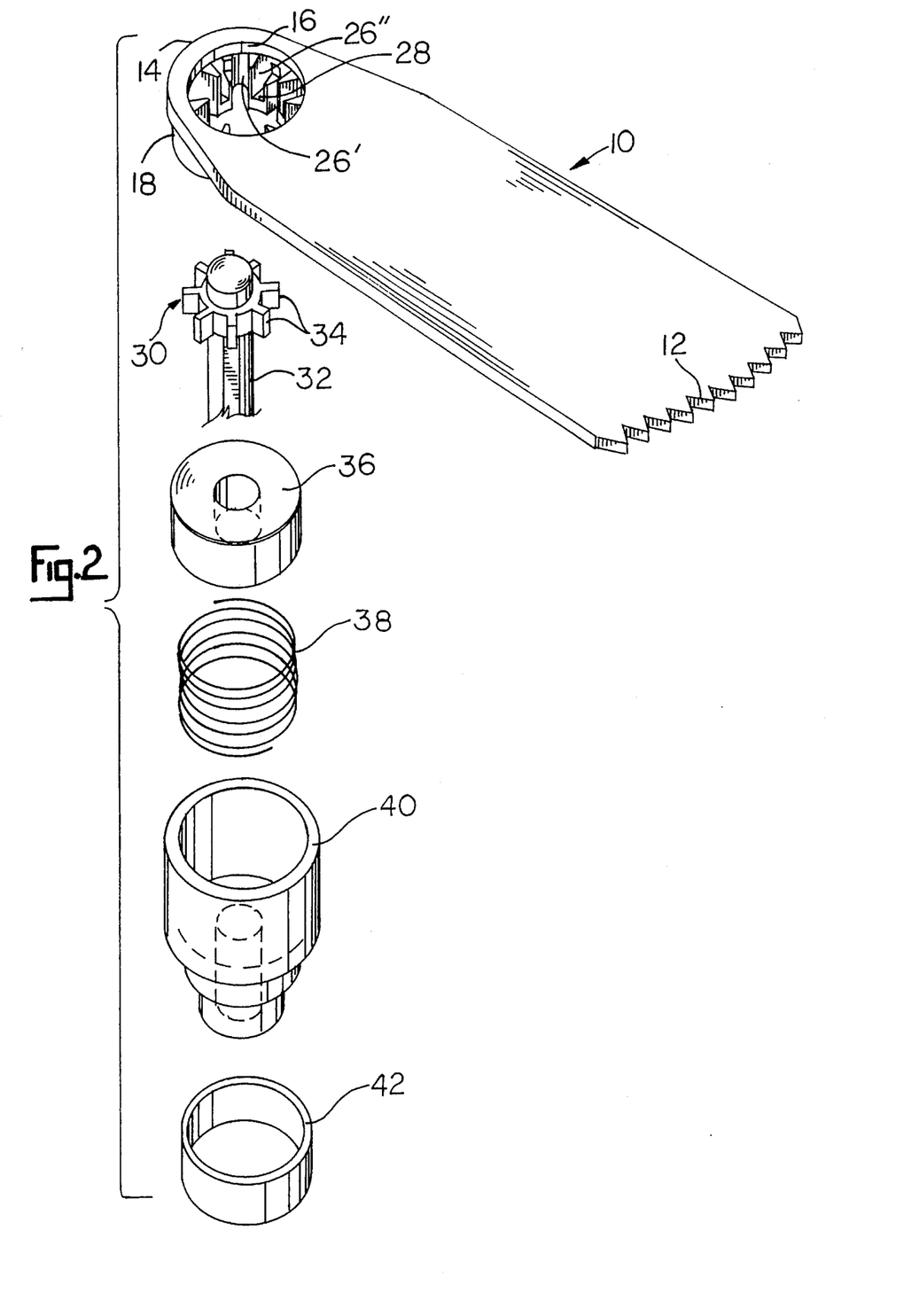
FIG. 2 is an exploded view of the blade and hub of the invention illustrating its component parts.
Figure 3:
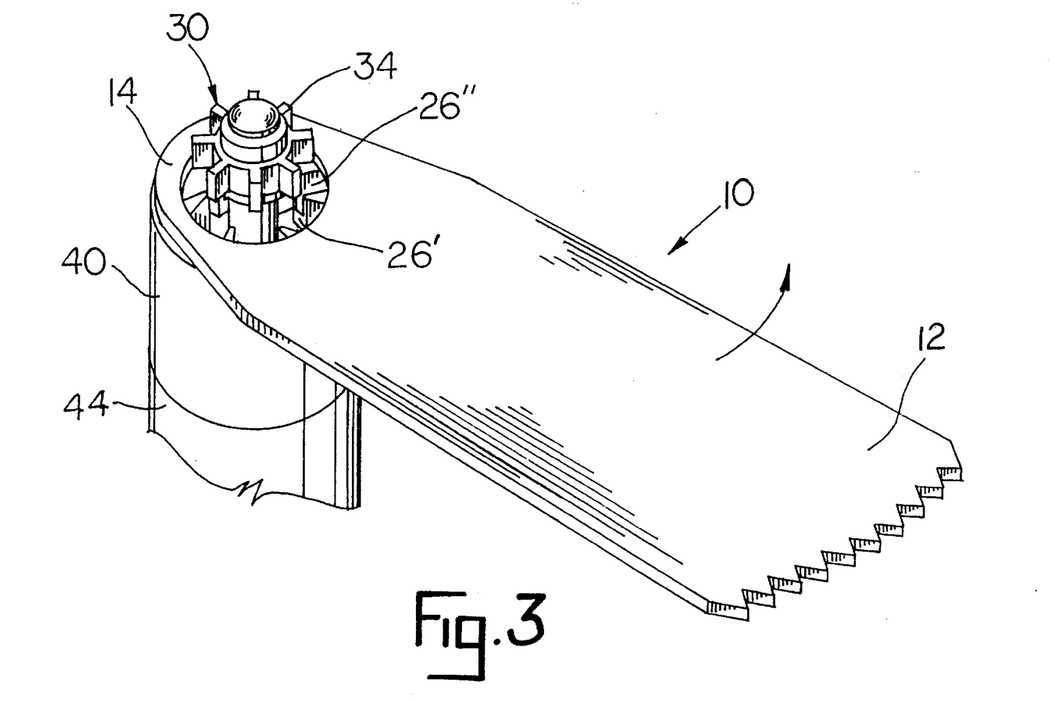
FIG. 3 is a perspective view of the blade and hub of the invention illustrating the blade pushed below the hub and rotatable into a locked position of FIG. 1.
Figure 4:
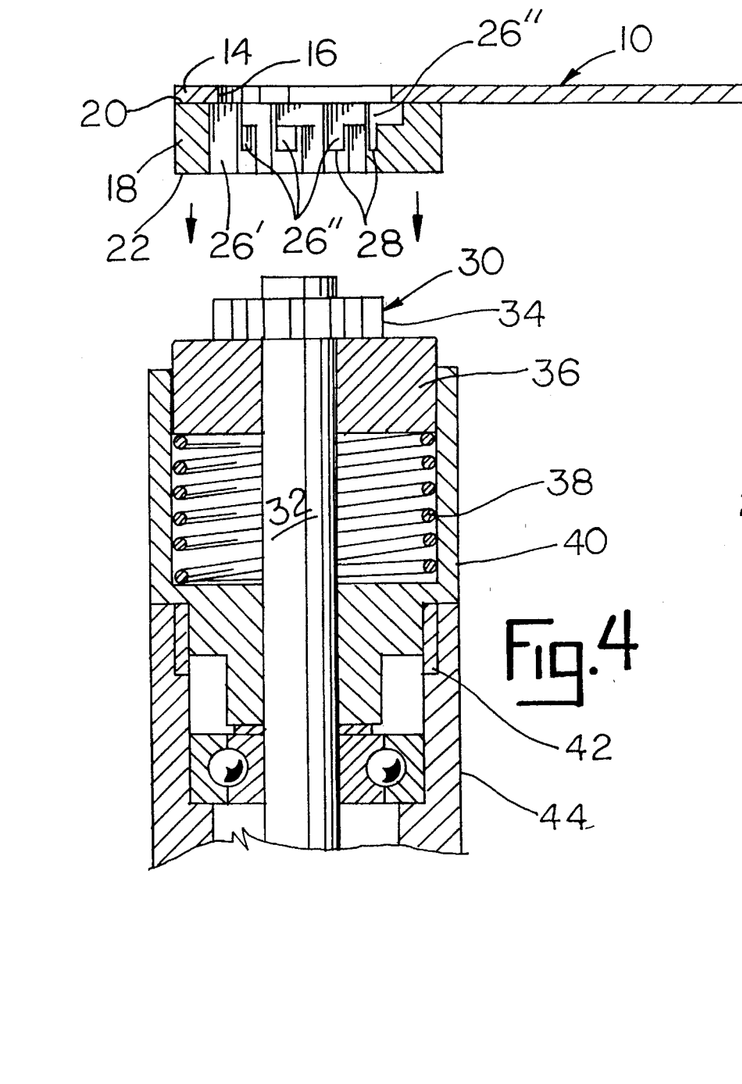
FIGS. 4 through 6 are side elevational views with portions sectioned which illustrate the steps involved in connecting or disconnecting a blade from the hub of the invention.
Figure 5:
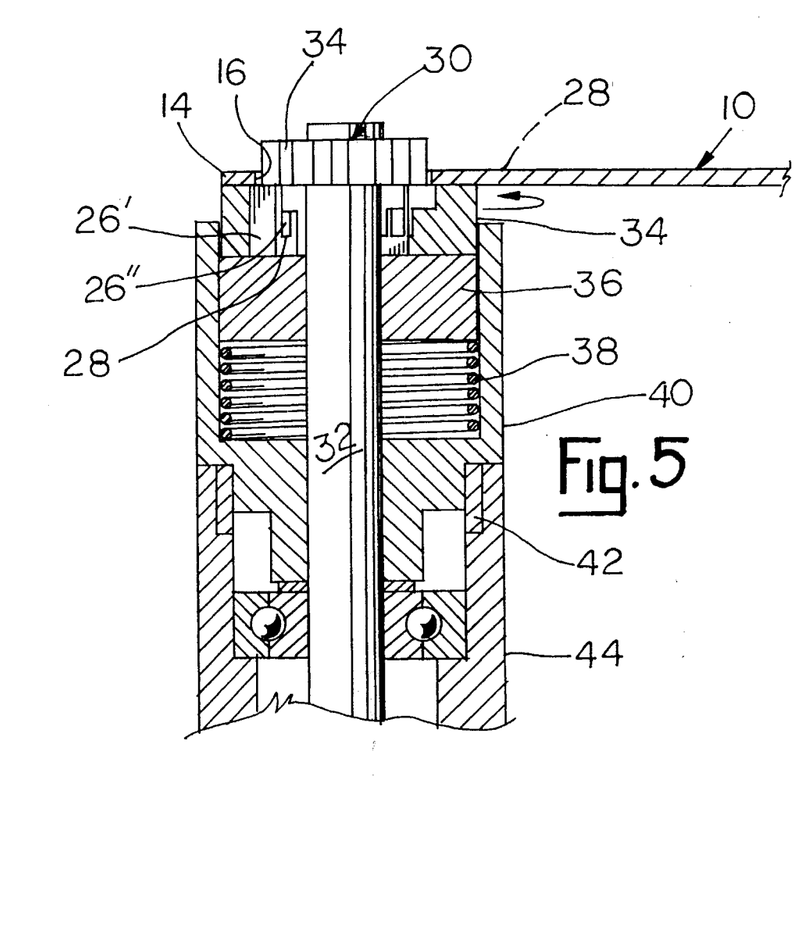
Figure 6:
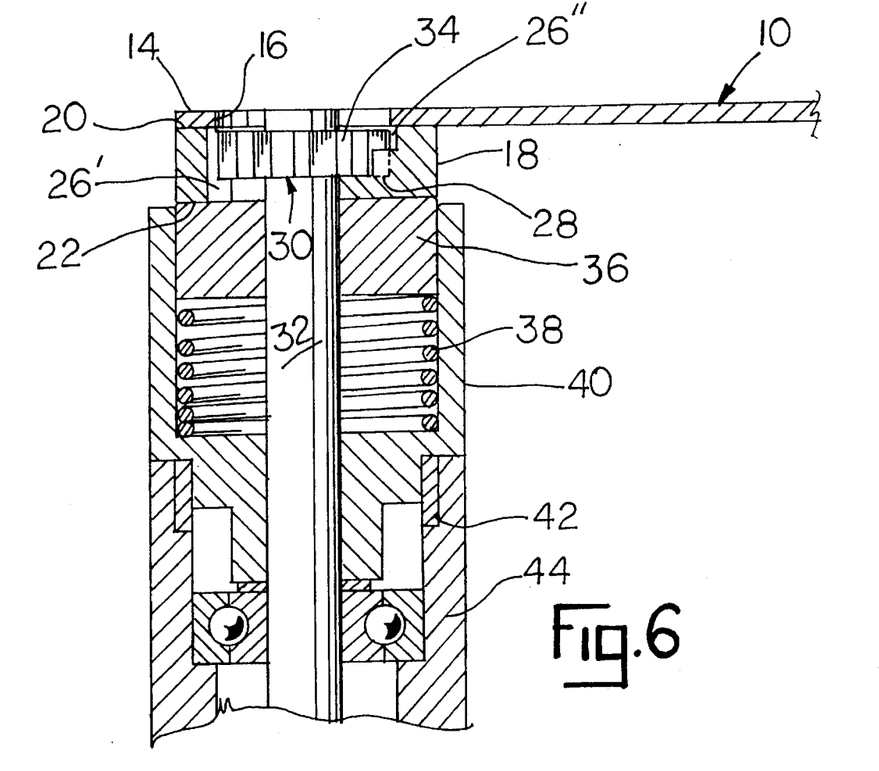
Figure 7:
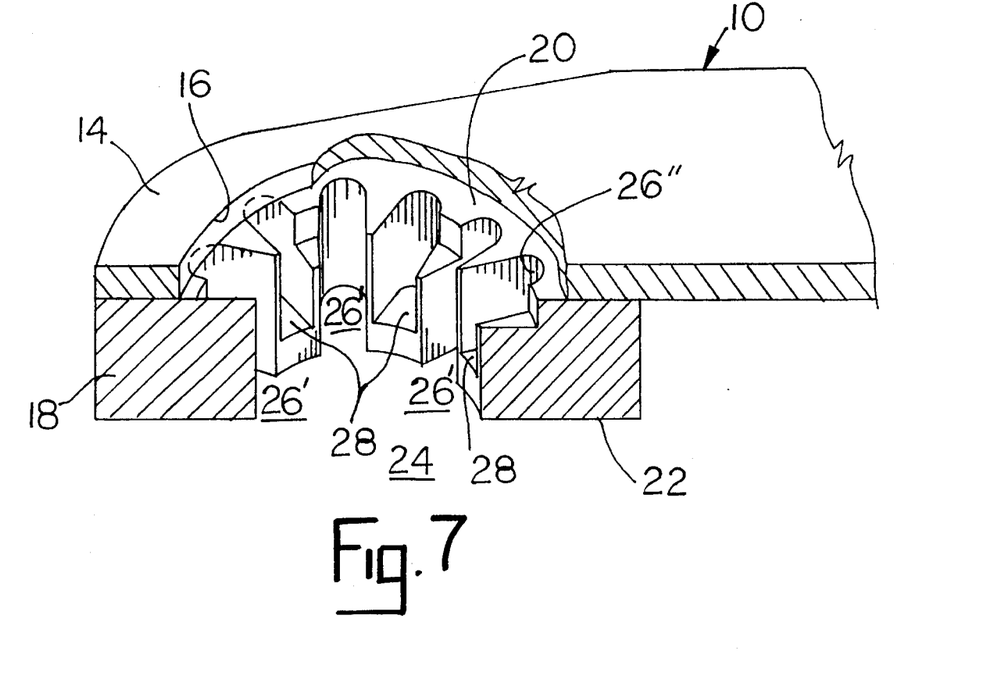
FIG. 7 is an enlarged partial view of the blade of the invention with portions sectioned for illustrative purposes.

The hub 30 is connected to a shaft 32 of a powered surgical instrument (not shown) of the type well known in the industry. It is sufficient for this part of the discussion merely to understand that shaft 32 oscillates about its longitudinal axis under influence of the powered surgical instrument. Hub 30 includes a plurality of fins 34 extending radially outwardly as illustrated in the figures. A pressure plate 36 is carried on shaft 32 and is slidable relative thereto. A helical spring 38 carried on shaft 32 biases plate 36 against hub 30. A spring housing 40, shaped as illustrated, is carried by the instrument with the shaft 32 extending through a central bore of the housing. Spring 38 is positioned between a portion of housing 40 and pressure plate 36 as shown. An annular outer race 42 is carried by the proximal end of housing 40 and is in contact with the housing 40 and the housing 44 of the orthopaedic instrument as shown in FIGS. 4 and 5.

To connect blade 10 to the powered surgical instrument, slots 26' are aligned with fins 34. Blade 10 is pushed onto shaft 32 and against plate 36 into the position illustrated in FIG. 5. It should be noted that in this position the interior surface 20 of washer 18 is spaced from the hub and spring 38 is substantially compressed. The blade 10 is rotated slightly relative to hub 30 (See FIG. 5) so that slots 26" are in alignment with fins 34. Blade 10 is released and urged by spring 38 and plate 36 toward hub 30 until shoulders 28 contact fins 34. (See FIG. 6) Spring 38 maintains pressure against plate 36 and blade during operation of the instrument. To disconnect blade 10 from the instrument, the blade is again pushed downwardly into the position of FIG. 5 and again rotated slightly until fins 34 are aligned with slots 26'. When the blade is release, spring 38 urges plate 36 and the blade toward hub 30. With the fins 34 aligned with slots 26', the blade is not inhibited by the hub and is pushed off of the hub by the force of spring 38.

Figure 8:
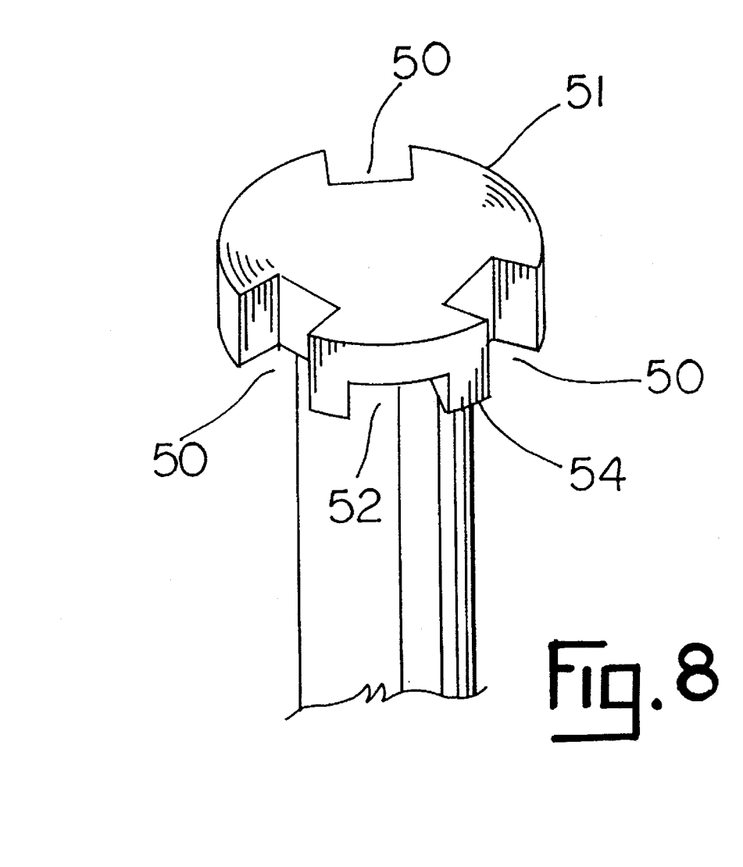
FIG. 8 is a perspective view of an alternative embodiment of the hub of the invention.
Figure 9:
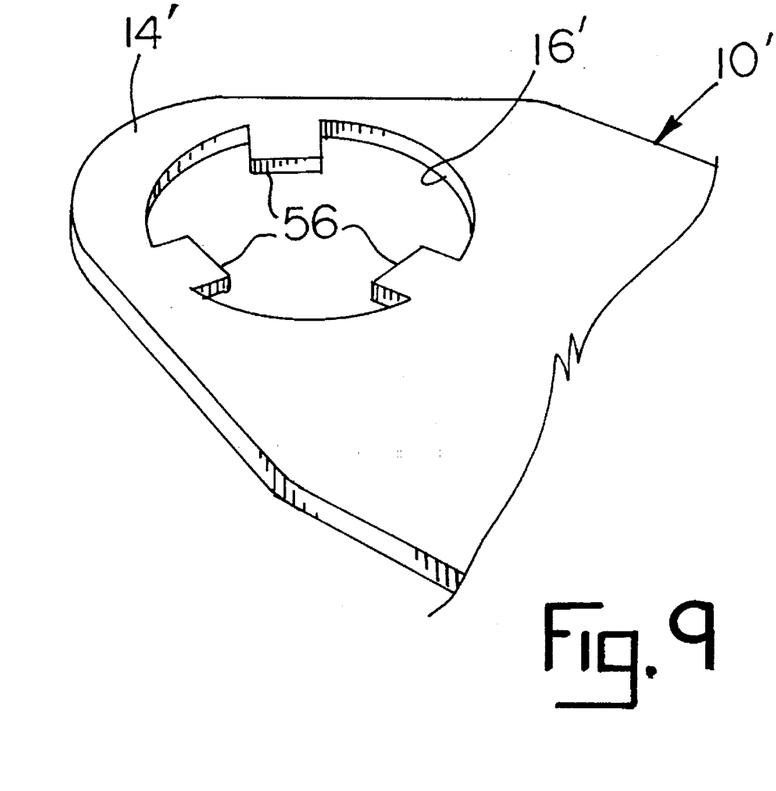
FIG. 9 is a partial perspective view of an alternative embodiment of the blade of the invention.
Figure 10:
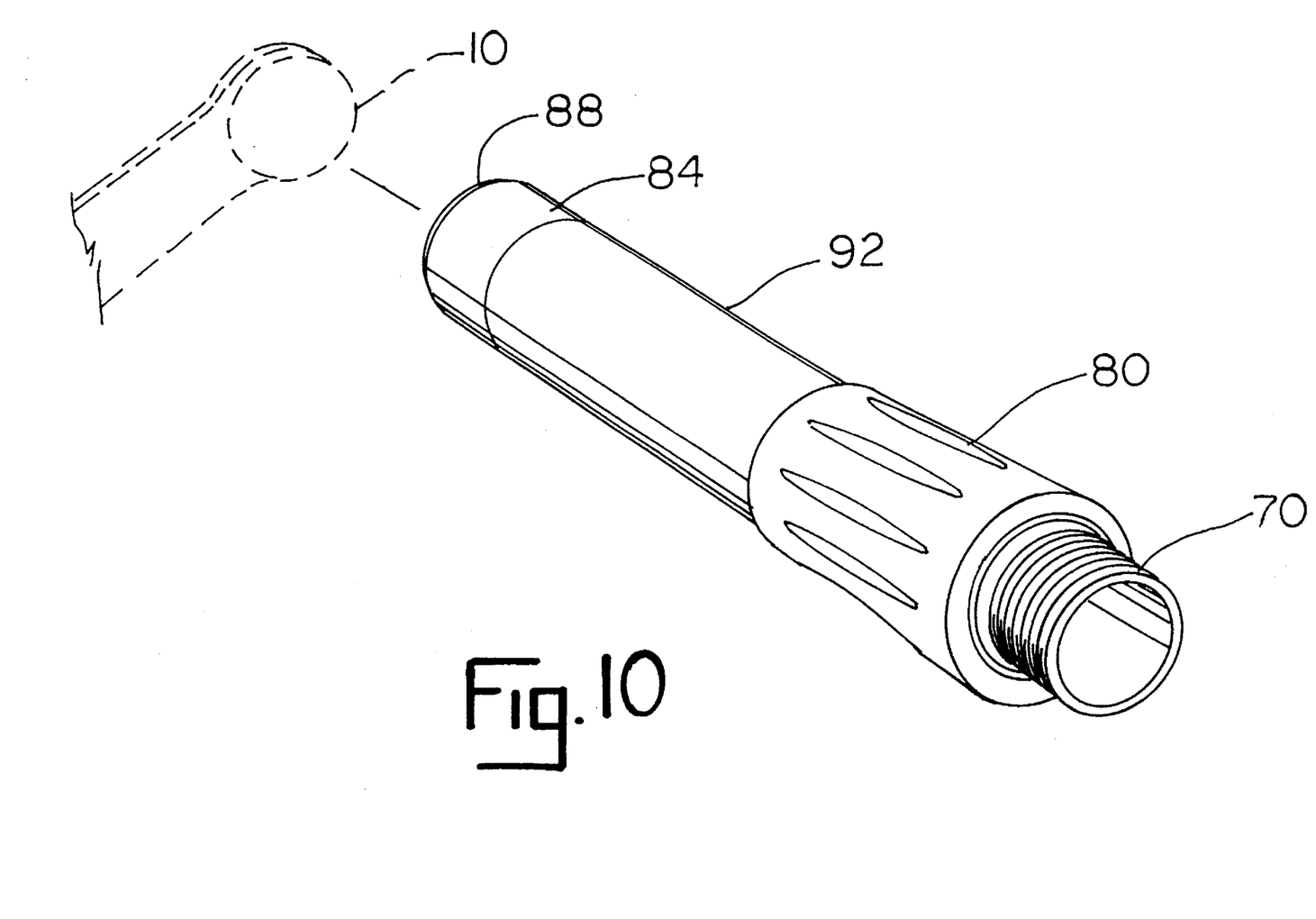
FIG. 10 is a perspective view of the preferred embodiment of the invention with a blade illustrated in broken lines.

An alternative embodiment is illustrated in FIGS. 8 and 9 wherein the hub 51 has a plurality of slots 50 formed radially about its periphery. Between each slot 50 an indentation 52 (only one shown) is formed extending from face 54 of the hub. Blade 10' is formed having a plurality of fins 56 extending into opening 16' end 14'. The alternative embodiment would also include a spring 38, pressure plate 36 and housing 40 as in the embodiment of FIGS. 1–7 but such components have not been illustrated for the sake of brevity. In use, to insert the blade 10' onto hub 51, fins 56 are aligned with slots 50 and the blade is pushed onto and beyond the hub. The blade is rotated until fins 56 are aligned with indentations 52 (only one shown) and the blade is released. When the blade is released, the spring and pressure plate (not shown) urges the blade into engagement with the hub in a similar manner as is fully described with reference to FIGS. 1–7.

Figure 11:
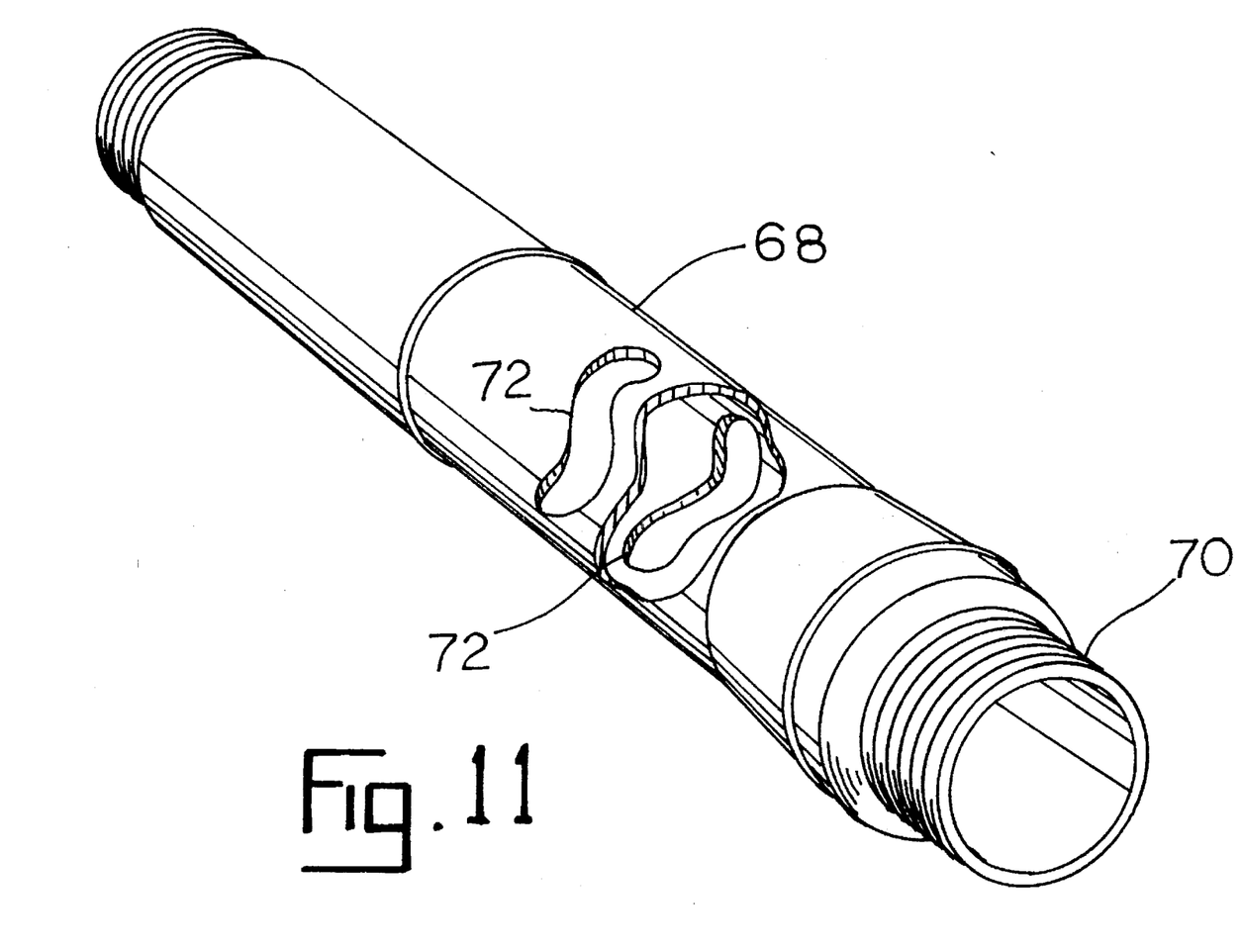
FIG. 11 is a perspective view of the housing of the preferred embodiment of FIG. 10 with portions broken away for illustrative purposes.
Figure 12:
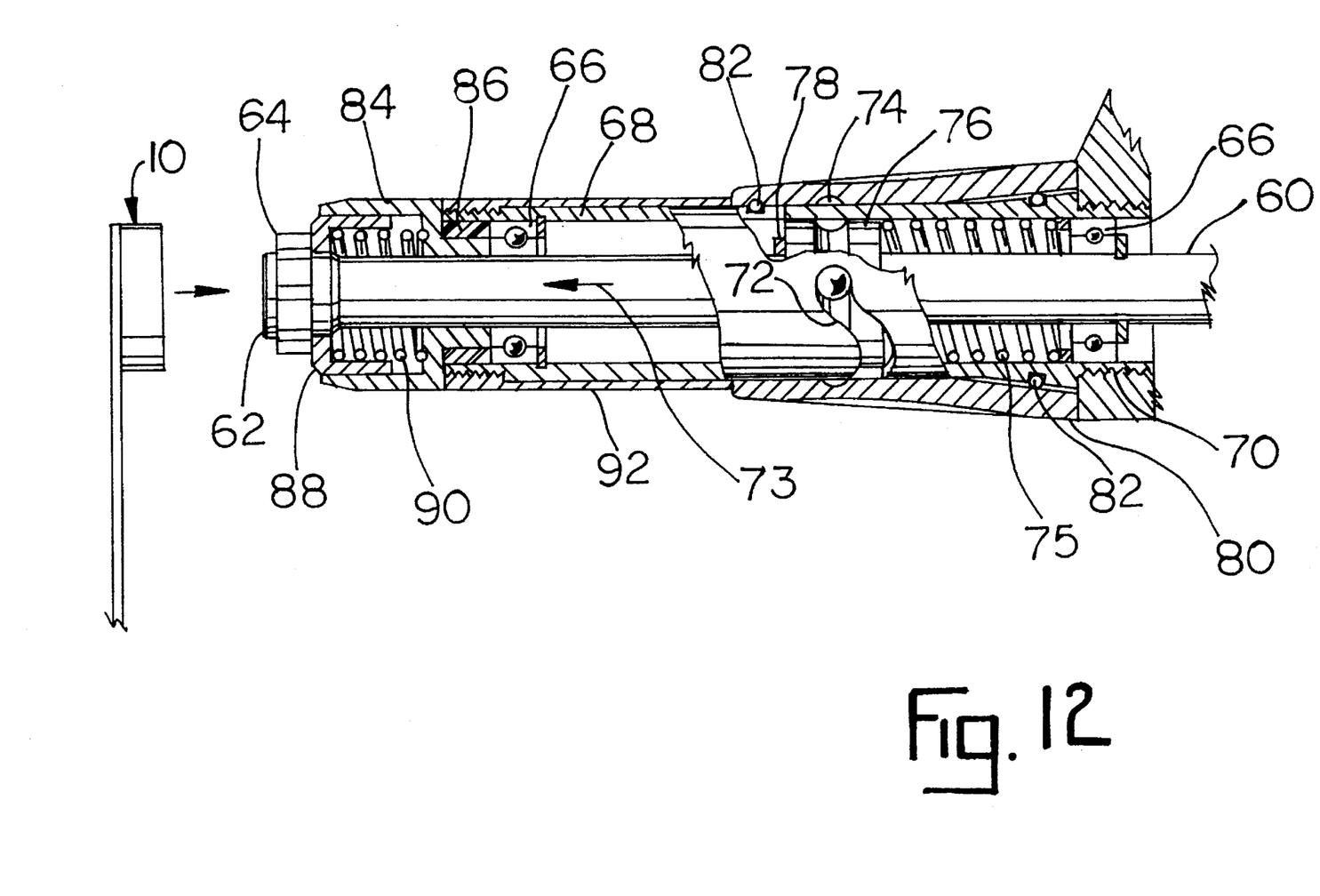
FIG. 12 is a sectional view of the preferred embodiment of the blade and hub of the invention with the drive shaft illustrated in an open position to accommodate the loading or unloading of a saw blade.
Figure 13:
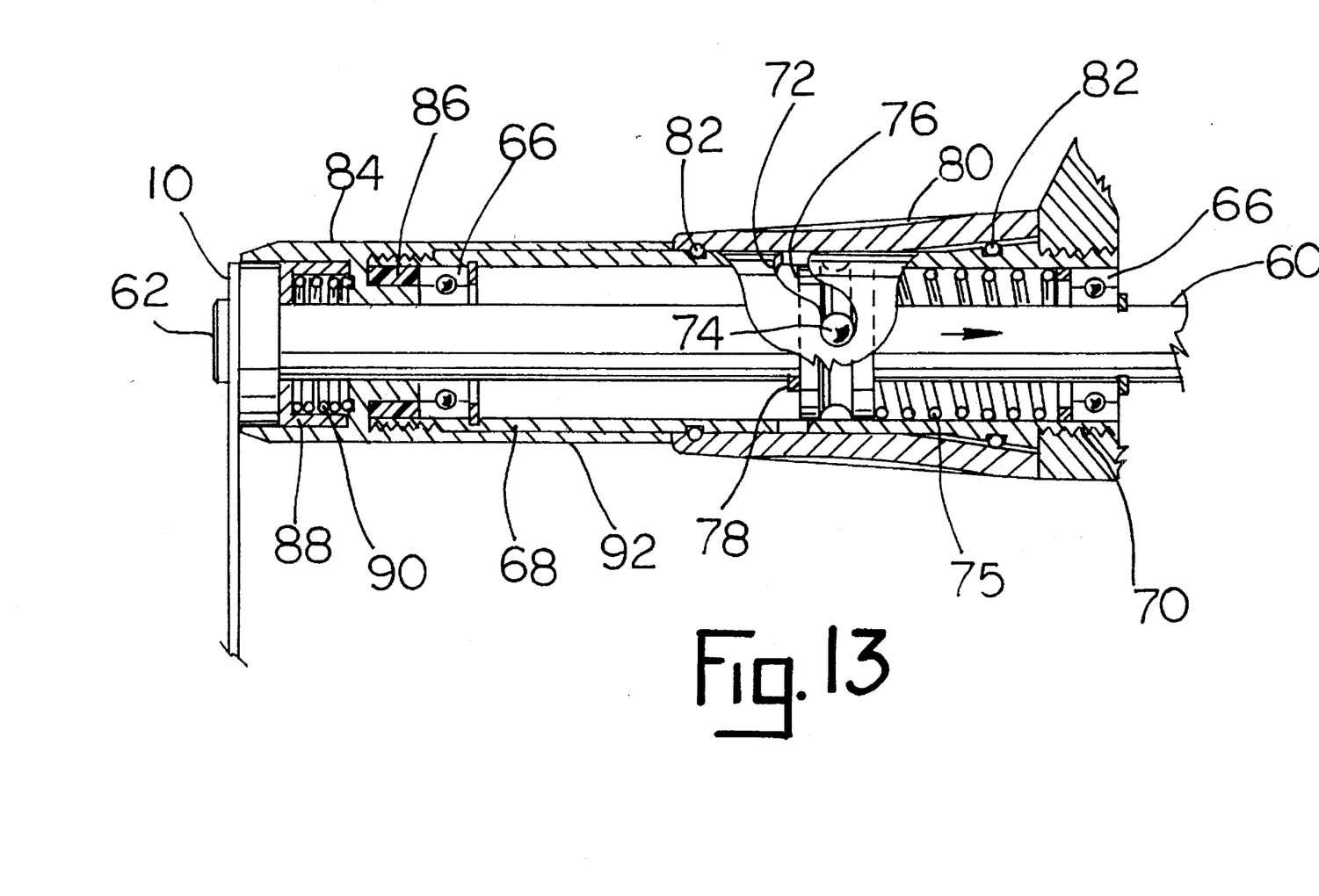
FIG. 13 is a sectional view of the preferred embodiment of the blade and hub of the invention with the drive shaft illustrated in a closed or locked position with a saw blade connected thereto.

The preferred embodiment of the invention is illustrated in FIG. 10 through 13 and is adapted for connection to a powered surgical instrument (not shown). The embodiment of FIGS. 10–13 includes a longitudinal drive shaft 60 having one end configured for connection to the drive mechanism of a powered surgical instrument and a distal end 62 having a hub 64. Hub 64 is substantially similar to hub 30 in form and operation to the hub of FIGS. 1–7 and need not be described further. Drive shaft 60 is rotationally supported by bearings 66 within cylindrical housing 68. End 70 of housing 68 is externally threaded to connect the housing to the powered surgical instrument (not shown). Housing 68 includes a pair of helical grooves 72 which accommodate a pair of balls 74. Grooves 72 are best illustrated in FIG. 11. Balls 74 ride within an annular groove formed in the periphery of a ball carrier 76. Drive shaft 60 extends through ball carrier 76 and is longitudinally fixed relative thereto by a retaining ring 78 which fits within an annular groove (not shown) of the drive shaft. A helical spring 75 is carried by the drive shaft between ball carrier 76 and a bearing 66 as illustrated and biases drive shaft 60 in the direction of arrow 73. A collet 80 is carried by housing 68 and is rotatable relative to the housing. Collet 80 includes a pair of arcuate recesses which accommodate a portion of balls 74 as illustrated in the drawings. A pair of o-rings 82 are carried by the housing and contact the inner surface of the collet as shown. A spring housing 84 is carried by the distal end of shaft 60 and is best illustrated in FIGS. 12 and 13. A seal 86 is positioned between a portion of the spring housing 84 and the inner surface of the housing 68. A pressure plate 88 is accommodated within spring housing 84 and also includes a central opening to accommodate a portion of the drive shaft. The central opening of the pressure plate is smaller than the hub to retain pressure plate 88 on the distal end of drive shaft 60. A helical spring 90 is carried between spring housing 84 and pressure plate 88 and biases the pressure plate away from the spring housing. An outer sleeve 92 is carried by housing 68 between collet 80 and spring housing 84.

FIGS. 12 and 13 illustrate the use of the embodiment of FIGS. 10–13 in association with the blade 10 as is described earlier. To connect or disconnect a saw blade from hub 64, collet 80 is rotated relative to housing 68. As balls 74 are partially captured within collet 80, rotation of the collet causes the balls to move about housing 68 within grooves 72. The balls are also partially captured within the annular groove formed in the ball carrier 66 which is fixed to drive shaft 60. Therefore, as the balls travel longitudinally along grooves 72, the ball carrier causes the drive shaft to shift along its longitudinal axis. This manner of converting a rotational movement into a lateral shift is known. With the drive shaft into the position of FIG. 12, the user may connect blade 10 onto hub 64 in the same manner as is described in FIGS. 1–7. As the user presses the blade onto the hub, pressure plate 88 compresses spring 90 and will hold pressure against the blade. To lock the blade onto the hub and prevent its accidental removal, the collet 80 is rotated in an opposite direction to cause the drive shaft to shift into the locked position of FIG. 13. In the locked position, the stronger spring 75 colapses spring 90, thus clamping hub 64 in blade 10.

It should be understood that the invention is not limited to the precise forms disclosed but may be modified within the scope of the appended claims.

We claim:

1. A locking mechanism for connecting a saw blade to a powered instrument, said mechanism comprising a hub carried by the powered instrument, said saw blade comprising a base end defining an aperture for accommodating a portion of said hub said hub and said blade having a plurality of interacting fins and slots, respectively, for locking the blade to the hub, said fins extending radially from the hub, the blade comprising a washer adjacent to the base end having an opening extending therethrough, the washer comprising an interior surface adjacent the blade and an exterior surface spaced from the blade, the plurality of complete slots extending radially from the opening into the washer, the complete slots extending from the interior surface to the exterior surface, a like plurality of truncated slots extending radially from the opening into the washer with a truncated slot being positioned between adjacent complete slots, the truncated slot extending from the interior surface toward the exterior surface and terminating spaced from the exterior surface thereby forming a shoulder.

2. The locking mechanism of claim 1 wherein said blade is inserted onto the hub in a first direction by aligning the fins with said complete slots and pushing the blade onto and beyond the hub, the blade is rotated slightly relative to the hub to align the fins with the truncated slots, the blade is biased opposite said first direction and said fins are accommodated within the truncated slots until said fins contact the shoulders of the truncated slots, the contact between said fins and the shoulders of the truncated slots constituting means for retaining the blade in contact with the hub.

3. The locking mechanism of claim 2 including a spring means carried by the instrument adjacent said hub for biasing said blade in said opposite direction.

4. In combination, a powered surgical instrument having a shaft with a hub connected thereto and a blade removably connected to the hub, the hub having a plurality of fins extending radially therefrom, the blade having a base portion with an opening therethrough, the base portion having first and second surfaces, a plurality of complete slots extend radially from the opening into the base portion, a like plurality of truncated slots extend radially from the opening into the base portion such that the truncated slots and the complete slots alternate about the opening, complete slots extending from the first surface to the second surface, the truncated slots extending from the first surface and terminating adjacent the second surface thereby forming a shoulder in each truncated slot, the complete slots accommodating the fins as said blade is pushed onto the hub and beyond the fins onto the shaft in a first direction, the truncated slots accommodating the fins such that the fins contact the shoulder of each truncated slot as the blade is urged in a direction opposite the first direction.

5. The combination of claim 4 further including a spring means carried by the shaft for biasing the blade in the opposite direction to maintain the fins in contact with the shoulders.

6. In combination, a powered surgical instrument having a shaft with a hub connected thereto and a blade removably connected to the hub, the hub having an outer surface, an inner surface and a periphery extending therebetween, a plurality of radial slots being formed in the periphery of the hub and extending from the outer surface to the inner surface, a like plurality of indentations being formed in the inner surface, an indentation being formed between an adjacent pair of slots, the blade having a base portion with an opening therethrough, a plurality of teeth extending radially into the opening, the slots of the hub accommodating the teeth of the blade as said blade is pushed onto and beyond the hub onto the shaft in a first direction, the indentations accommodating the teeth such that the teeth fit into each indentation as the blade is urged in a direction opposite the first direction.

7. The combination of claim 6 further including a spring means carried by the shaft for biasing the blade in the opposite direction to maintain the teeth in contact with the indentations.

8. A surgical saw blade comprising a toothed portion and a base portion with an opening therethrough, the base portion having first and second surfaces, a plurality of complete slots extend radially from the opening into the base portion, a like plurality of truncated slots extend radially from the opening into the base portion such that the truncated slots and the complete slots alternate about the opening, complete slots extending from the first surface to the second surface, the truncated slots extending from the first surface and terminating adjacent the second surface thereby forming a shoulder in each truncated slot.

9. A surgical saw blade comprising a toothed end and a base portion, a circular opening formed in the base portion for accommodating the hub of a powered surgical instrument, a plurality of radial teeth extending into and evenly annularly spaced around the circular opening configured for engagement within radial slots formed in the hub.

* * * * *